United States Patent [19]

Wade

[11] Patent Number: 4,905,898
[45] Date of Patent: Mar. 6, 1990

[54] COMBINED BOX AND BAG PACKAGE FOR ROOM FRAGRANT POTPOURRI

[75] Inventor: Phillip C. Wade, Heber Springs, Ark.
[73] Assignee: Aromatique, Inc., Heber Springs, Ark.
[21] Appl. No.: 198,834
[22] Filed: May 26, 1988
[51] Int. Cl.⁴ .............................................. A61L 9/04
[52] U.S. Cl. ...................... 239/6; 220/403; 220/404; 239/55; 239/57; 239/58
[58] Field of Search .......................... 239/6, 34, 55-58, 239/60; 220/403, 404; 229/162

[56] References Cited

U.S. PATENT DOCUMENTS

| | | | |
|---|---|---|---|
| 1,758,347 | 5/1930 | Beiben | 239/60 |
| 2,738,224 | 3/1956 | Turner et al. | 239/57 |
| 2,766,067 | 10/1956 | Shinberg | 239/58 |
| 2,809,863 | 10/1957 | Curran | 239/57 |
| 3,039,648 | 6/1962 | Busch | 220/404 |
| 3,065,915 | 11/1962 | Samann | 239/58 |
| 3,119,543 | 1/1964 | Walker | 220/404 |
| 3,424,380 | 1/1969 | Curran | 239/58 |
| 3,576,290 | 4/1971 | Marchisen | 220/404 |

FOREIGN PATENT DOCUMENTS

| | | | |
|---|---|---|---|
| 2558697 | 8/1985 | France | 239/57 |
| 6601120 | 8/1967 | Netherlands | 239/34 |
| 2073020 | 10/1981 | United Kingdom | 239/34 |

Primary Examiner—Andres Kashnikow
Assistant Examiner—Michael J. Forman

[57] ABSTRACT

An aesthetically enhanced carton having an opening in one wall through which the open top of a bag is laced or threaded enabling the bag to be supported and enclosed within the carton while communicating the interior of the bag and the exterior of the carton through a passage extending through the neck of the bag. When used with room fragrant potpourri, the scent of the potpourri is controllably released to the ambient.

12 Claims, 2 Drawing Sheets

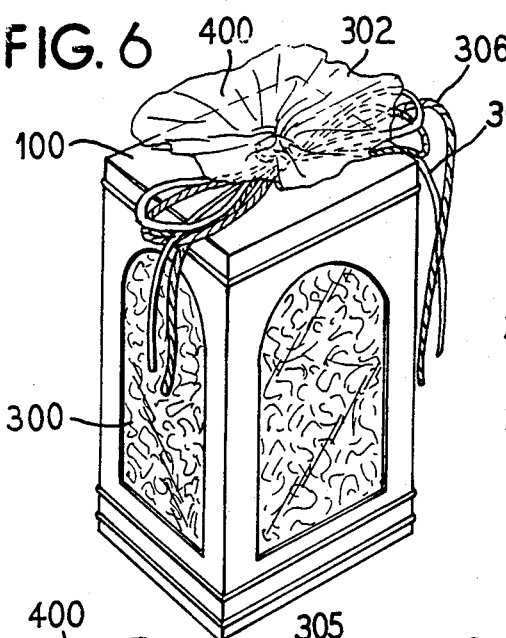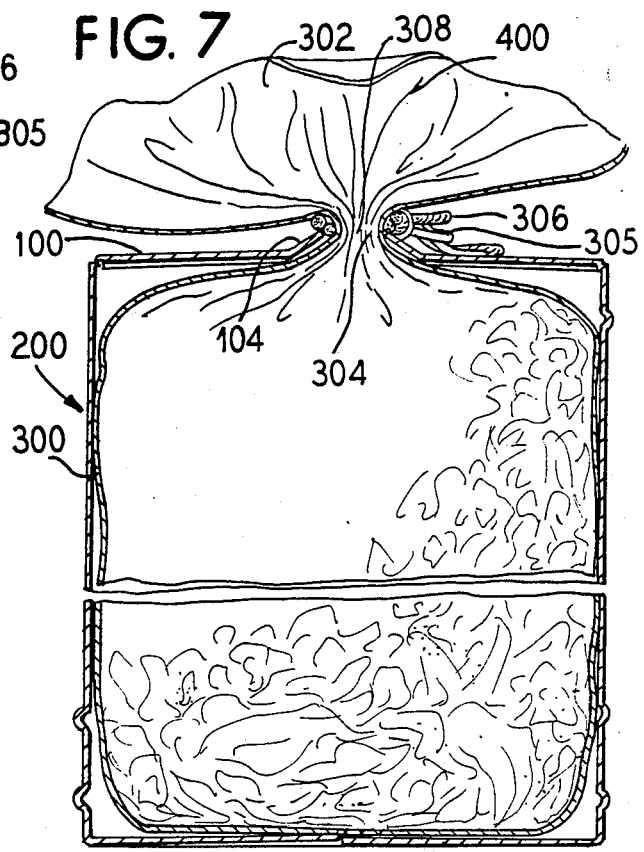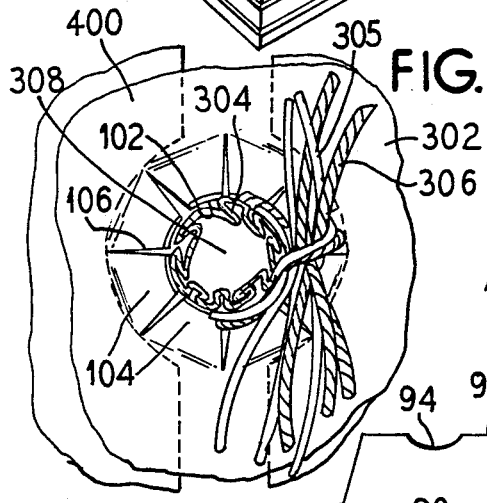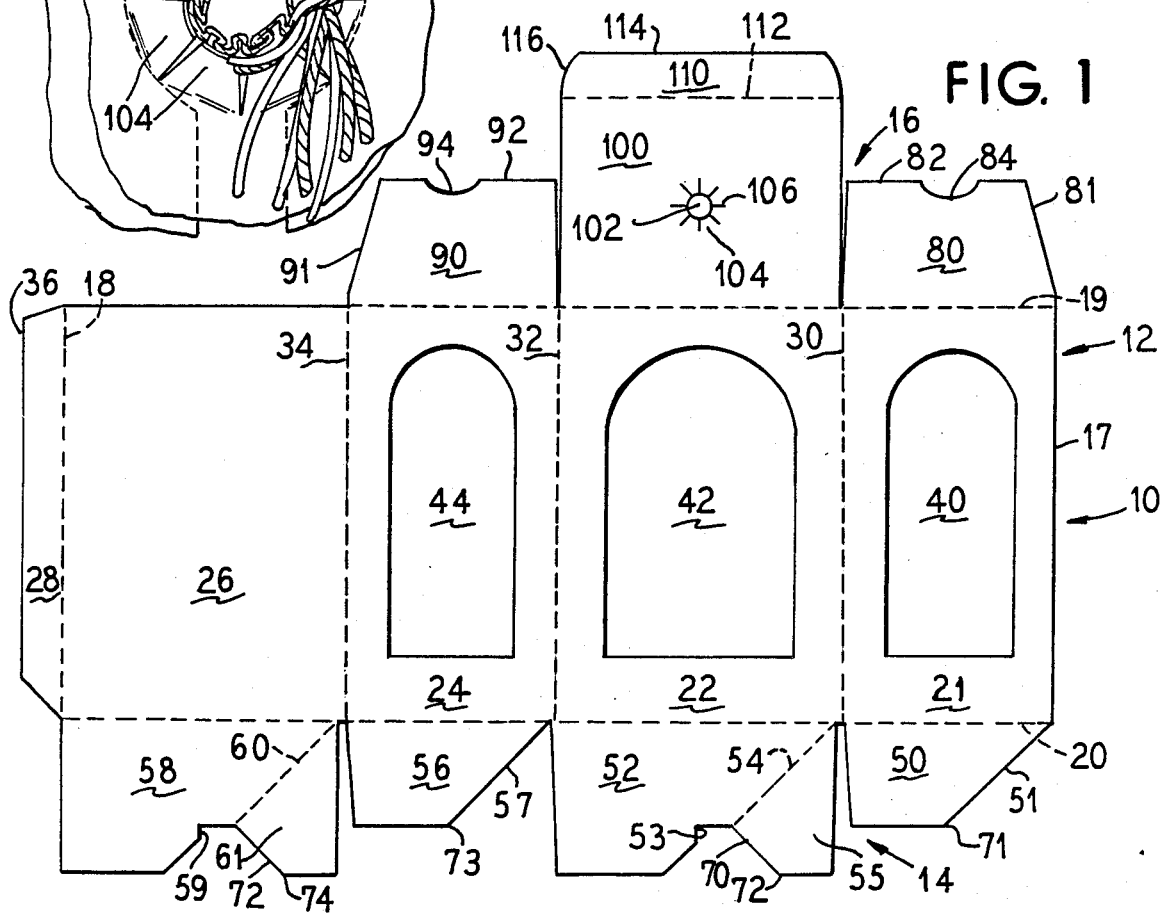

4,905,898

COMBINED BOX AND BAG PACKAGE FOR ROOM FRAGRANT POTPOURRI

BACKGROUND OF THE INVENTION

1. Field of the Invention

The present invention is directed generally to carton construction and particularly to a carton and a method of making the same for packaging room fragrant potpourri.

2. Description of the Prior Art

The state of the prior art is exemplified by a form of packaging in current usage. Applicant's assignee has heretofore packaged decorative room fragrant potpourri in a distinctive trade dress which is the subject matter of formal trademark registrations and wherein the trade dress of the mark is described as a full packed rectangularized pillow-shaped bag having transparent walls through which the goods may be viewed and the top open end of the bag is gathered to form a pleated crown above a closed neck secured by a decorative colored rope-like cord tied in a square-bow knot and a colored oval indicia-bearing label is affixed to the interior surface so as to be visibly centered in a rectangular front wall panel.

SUMMARY OF THE INVENTION

In accordance with the principles of the present invention, a carton is provided which is made of chip board or some suitable form of paper stock so that the carton displays the requisite characteristics of stiffness that the package is definitely rectangularized, thereby facilitating packaging, shelving and storage of multiple units.

Further, the carton is designed to have ample display windows so that the product within the carton and which may advantageously be included within a generally pillow-shaped bag as exemplified by the prior art and may be readily viewed through two or three sides of the carton.

In accordance with the principles of the present invention, the carton is provided with a unique closure system in its top extremities so that the bag and the carton may be integrated in a particularly artistic and functionally aesthetic manner. More particularly, the top open end of the bag is gathered to form a pleated crown. However, by the present invention, the pleated crown is threaded through a customized opening formed in the top portions of the carton. Thus, a neck of the bag extends through an opening in the carton and the pleated crown of the bag is disposed in a very pleasing array on the top of the carton.

Since the neck of the bag is not tightly closed, a limited opening or throat extends through the neck of the bag and through the opening of the carton, thereby releasing a limited mount of the fragrance of the room fragrant potpourri.

BRIEF DESCRIPTION OF THE DRAWINGS

FIG. 1 is a development view of a sheet form body provided in constructing the carton of the present invention;

FIG. 6 is a front perspective view of the completed carton;

FIG. 7 is a cross-sectional view of the carton with parts broken away taken along the lines VII—VII of FIG. 6 and showing additional details of construction;

FIG. 8 is a fragmentary top plan view of the completed carton.

DETAILED DESCRIPTION OF THE PRESENTLY PREFERRED EMBODIMENT

Figure 2:
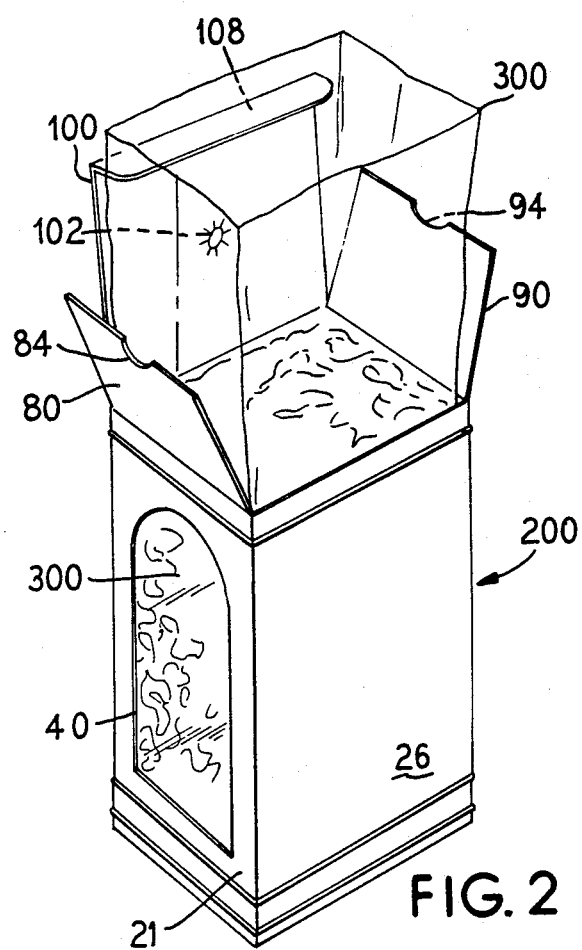
FIG. 2 is a rear perspective view of the carton in an initial stage of assembly and with a bag containing potpourri inserted therein.

In FIG. 1, there is shown a sheet-form body 10 utilized in forming a carton 200 shown in various stages of assembly in perspective in FIGS. 2-6 in accordance with the invention. The sheet-form body 10 is cut, scored, embossed and perforated to provide a panel section 12, a bottom flap section 14 and a top flat section 16. For example, the carton can be made of chip board which is readily die cut, or of any comparable material exhibiting a requisite degree of stiffness so that the carton will lend itself readily to storage, stacking and shelving. Moreover, it is highly desirable to select a material that can be coated and/or imprinted or glazed to provide an enhanced decorative appearance. In one embodiment of the invention, the body 10 is coated on the entire side visible in FIG. 1 with an attractive metallic silver coating.

The panel section 12 is rectangular in form and is bounded by a panel section right edge 17, left edge 18, top edge 19, and bottom edge 20. The edges 18, 19 and 20, shown as dashed lines, are formed by scoring or embossing creases in the sheet-form body 10. As is discussed below, the sheet-form body 10 is bent along these and other embossed and perforated edges to form the assembled carton 200. Furthermore, as will become evident, upon assembly of the carton 200, the edges 17 and 18 are positioned vertically and the edges 19 and 20 are positioned horizontally.

Edges 30 and 32 and 34, running perpendicular to the panel section top edge 19 to the panel section bottom edge 20, are also formed by scoring or by embossed creases to subdivide the panel section 12 into a first side panel 21, a front panel 22, a second side panel 24 and a back panel 26. The panels 21, 22, 24 and 26 cooperate to form the four vertical faces or sides of the carton 200.

The first side panel 21 is bounded by the edges 17, 19, 20 and 30. The front panel 22 is formed adjacent to and to the left of the first side panel 21 and is bounded by the edges 19, 20, 30 and 32. The second side panel 24 is formed to the left of and adjacent to the front panel 22 and is bounded by the edges 19, 20, 32 and 34. Finally, the back panel 26 is formed adjacent to and to the left of the second side panel 24 and is bounded by the edges 18, 19, 20 and 34.

A back panel tab 28 is formed to the left of the back panel 26 (using the orientation of FIG. 1) and is connected thereto along the embossed edge 18. Upon assembly of the carton 200, the outer surface of the back panel tab 28 is secured to the inner surface of the first side panel 21, preferably by an adhesive. Thus, upon assembly of the carton 200, the edges 18, 30, 32 and 34 form and define the vertical right angled edges of the carton 200.

The panels 21, 22 and 24 also include windows 40, 42 and 44, respectively. The windows 40, 42 and 44 are included to allow product, which in the preferred embodiment is a bag of potpourri, placed within the carton 200 to be seen. The windows 40, 42 and 44 are shown as being arched and proportionally dimensioned according to the sizes of the respective panels to provide an aesthetically pleasing appearance to the carton 200. Of course, the windows 40, 42 and 44 can be formed of any selected geometrical shape.

The bottom of the carton 200 is defined by bottom flaps which comprise the bottom flap section 14. Each of the panels 21, 22, 24 and 26 has connected to it a bottom flap along the panel section bottom edge 20 which cooperates with the other bottom flaps so that upon assembly of the carton 200, the flaps will define a collapsible carton bottom.

Similarly-shaped bottom flaps 50 and 56 are formed below the first side panel 21 and second side panel 24, respectively. Each of the bottom flaps 50 and 56 includes an angled edge 51 and 57, respectively.

Additionally, similarly-shaped bottom flaps 52 and 58 are formed below the front panel 22 and back panel 26. The bottom flaps 52 and 58 include notch portions 53 and 59, respectively; and overlapping flap sections 55 and 61, respectively.

Upon assembly of the carton 200, the bottom flaps 50, 52, 56 and 58 are connected together to form a collapsible bottom for the carton 200. The bottom flap 50 is connected to the bottom flap 52 such that the outer surface of the bottom flap 50 is secured to the inner surface of the bottom flap 52. Specifically, the edge 51 of the bottom flap 50 is aligned with an edge 70 of the overlapping flap section 55. Corners 71 and 72 register with each other. Because the bottom flap 52 includes the perforated edge 54, the connected bottom flaps 50 and 52 will fold along the edge 54 upon collapse of the carton 200 when it is empty.

The bottom flaps 56 and 58 are similarly connected, the edges 57 and 72 being aligned and the corners 73 and 74 being in register.

The notch portions 53 and 59 engage upon assembly of the floor or bottom of the carton 200 and prevent collapse or folding of the bottom or floor by frictional interaction between the notch portions.

Above the first and second side panels 21 and 24 are formed top flaps 80 and 90, respectively, the top flaps 80 and 90 being connected to the side panels 21 and 24 along the panel section top edge 19 and therefore, foldable therealong. As can be seen in FIG. 1, the top flaps 80 and 90 are formed symmetrically about a lid 100 which is formed above the front panel 22. The top flaps 80 and 90 include respective angled edges 81 and 91, the angles of which permit easier insertion of a lid tab 110 connected to the lid 100 and which serve to retain the lid tab 110 once it has been inserted to close the lid 100.

Figure 3:
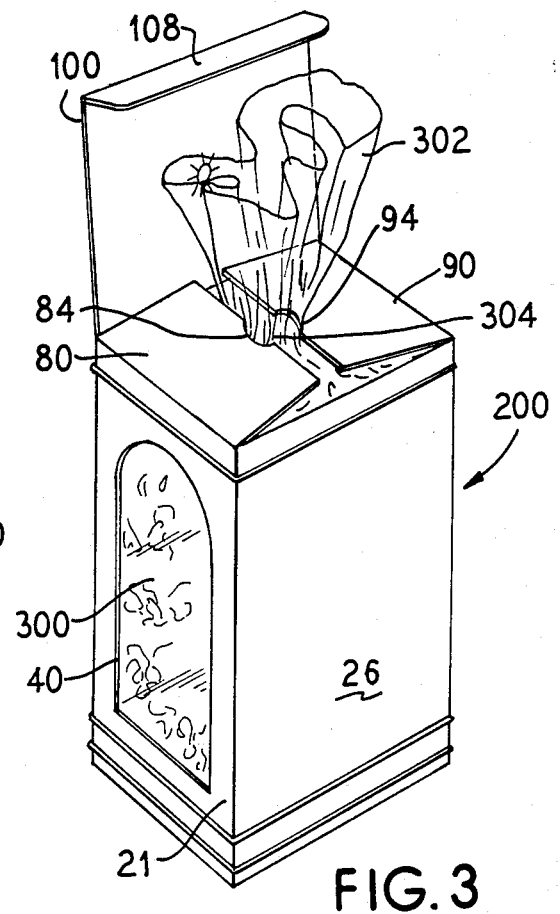
FIG. 3 is a view similar to FIG. 2, but in a further stage of assembly.

The top flaps 80 and 90 also include top flap edges 82 and 92, respectively. In accordance with this invention and as is shown in FIGS. 1, 2 and 3, the top edges 82 and 92 are formed to include semicircular cut-outs 84 and 94, respectively. The cut-outs 84 and 94 are medially disposed notches or recesses and are aligned with one another so that upon closing or folding down of the top flaps 80 and 90, in an assembled carton 200, the cut-outs 84 and 94 register with each other to form a circular through-opening as is best shown in FIG. 3.

In accordance with this invention, the lid 100 formed above the front panel 22 is provided with a centrally located opening 102 adapted to be disposed in aligned registry with the opening formed by the recesses or cut-outs 84 and 94 and such opening is generally positioned at the approximate center of the rectangular top panel formed by the lied 100.

While the opening 102 may be formed in various ways by punching, cutting or die cutting, the exemplary form of the invention herein illustrated and described is die cut so that the hole portion may be pushed out when the carton is ready for use. Surrounding the opening 102 are slits 106 extending radially outwardly from the hole 102 and together with one another forming a plurality of tabs 104 which allow the periphery of the opening 102 to be flexible and selectively expandable.

Starting with the sheet-form body 10 of FIG. 1, the body is formed into a tube by folding the panels at the score lines or creases 30, 32 and 34 and the tab 28 is adhesively engaged with one surface of the panel 21.

The bottom end of the now tubular body 10 is closed by interweaving the flaps and tabs 50, 52, 56 and 58.

Referring now to FIG. 2, the partially assembled carton is ready to receive a bag 300 which may already be partially charged with a quantity of fragrant potpourri. At the stage of assembly illustrated in FIG. 2, the remaining charge of potpourri may be filled through the top open mouth of the bag 300.

It is contemplated by the present invention that the bag 300 will be made of transparent material so that the contents of the bag 300 can be viewed through the walls of the bag. Either a plastic material may be utilized or cellophane or some suitable material having comparable characteristics is utilized.

Referring now to FIG. 3, the top portion 302 of the bag 300 is gathered to form a neck 304. Thus, when the flap 80 is folded over to overlie the top of the bag 300 and the flap 90 is likewise folded over to overlie the top of the bag 300, the recesses or cut-outs 84 and 94 respectively will receive and enclose the neck 94. Further, the top of the bag 302 is laced through the opening 102 as is more specifically shown in FIG. 4 wherein the lid 102 is shown positioned superjacent the bag 300 and the assembled carton. As the top 302 of the bag 300 is treaded through the opening 102, the ribs or tabs 104 will tend to closely embrace the neck of the bag 304 and the lid 102 can be successively moved downwardly until the tab 108 is inserted inwardly adjacent the rear wall 26 of the carton so that the assembly of the carton is relatively complete.

Although each of the cut-outs 84 and 94 is shown as having a semicircular periphery, other shapes can be provided within the spirit and scope of the invention. For example, the periphery of each of the cut-outs 84 and 94 can be rectangularly-shaped or triangularly-shaped. It is important only that the cut-outs 84 and 94 define a hole about the neck 304 of the bag 300 when the top flaps 80 and 90 are folded down.

Figure 4:
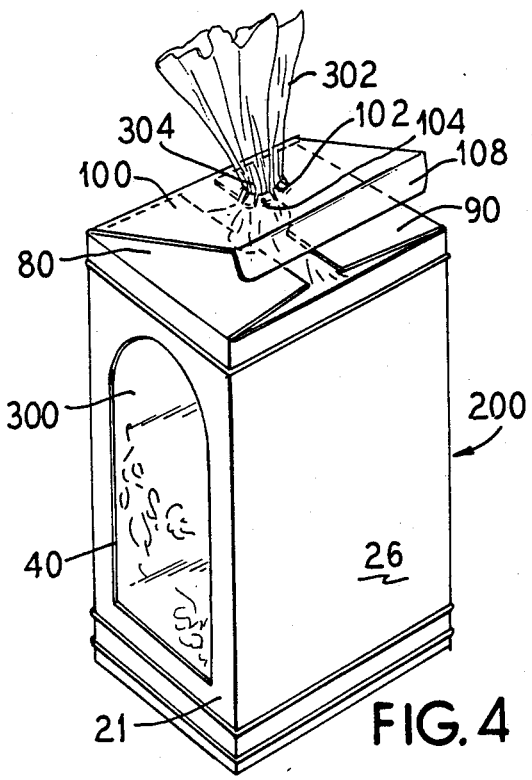
FIG. 4 is a view similar to FIGS. 2 and 3 in a still further stage of assembly.

As shown in FIG. 4, the tabs 104 surrounding the opening 102 are shown slightly uplifted as the top portion 302 of the bag 300 is pulled through the opening 102. The presence of the tab structure around the opening 102 permits the hole opening to be somewhat flexible as the top portion 302 of the bag 300 is threaded therethrough. Once enough of the top portion 302 of the bag 300 has been threaded through the hole 102, the tabs 104 hinder or impede retraction of the top portions 302 back into the carton 200.

Figure 5:
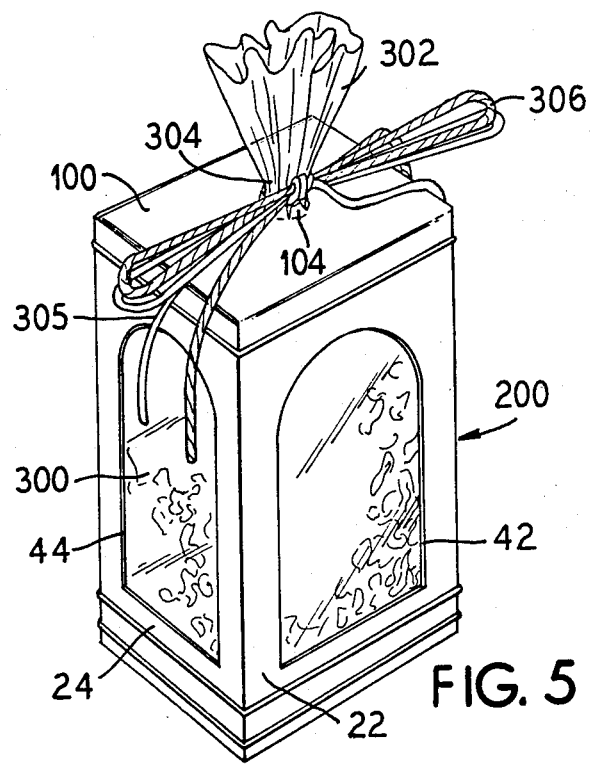
FIG. 5 is a front perspective view of the carton of FIGS. 2, 3 and 4 in a final stage of assembly.

Referring now to FIG. 5, the completed carton, the appearance of the carton may be selectively enhanced by the use of one or more bows. For example, as shown in FIG. 5, a pair of separate bows are utilized including a first cord 305 which in this embodiment is a thin silver cord matched to the color of the coating on the carton 10 and the second cord is a thicker rope-like cord 306. Both of the cords 305 and 306 are tied with a bow knot around the neck 305 of the bag and the gathered top portion of 302 of the bag 300 is then pleated and flattened to produce a pleated skirt 400 which overlies the decorative bowed cords 305 and 306 as well as the lid 102 of the carton 10.

The cooperative combination achieved by the neck 304 of the bag 300 closely encircled by the tabs 104 surrounding the opening 102 in the lid 100 forms a passage 308 extending through the neck 304 of the bag and opening out of the center of the pleated skirt 400. Thus, a limited amount of fragrance from the fragrant potpourri within the bag 300 may escape through the passage 308 so that the carton packaging of the potpourri achieves a highly pleasing dual impact upon both the visual and olfactory senses.

The passage 308 down through the inside of the neck 304 of the bag 300 is preferably left unimpeded by the tightness of the bows formed in the cords 305 and 306 tied about the neck 304 of the bag 300. Thus, the passage 308 provides a controlled metering for the fragrances of the potpourri contained within the bag 300 which can be enjoyed and smelled by potential purchasers of the potpourri.

Simultaneously, the potpourri is packaged in a firm rectangular box-like container which lends itself to facile storage in shipping cartons and may also be shelved and otherwise stacked in open displays within a retail establishment so that the package creates a particularly pleasing aesthetic appearance and also creates it own aura of pleasant scent to create an attractive retailing ambience.

Although various minor modifications might be suggested by those versed in the art, it should be understood that I wish to embody within the scope of the patent warranted hereon all such modifications as reasonably and properly come within the scope of my contribution to the art.

I claim as my invention:

1. A combined carton and bag package for room fragrant potpourri comprising:
    a sheet-form member cut, scored and shaped to form
        a rectangular tube having a bottom and a top,
        a bottom wall closing said bottom of said tube;
    a lid selectively closing the top of said tube;
    a potpourri bag filled with fragrant potpourri in said carton and having an open top gathered to form a confined neck in the bag,
        said lid having a restricted opening therein through which the gathered neck of the bag is laced;
    said neck having a passage extending from the interior of the bag to the ambient exteriorly of the carton; and
    a supply of room fragrant potpourri within the bag and emitting scent through said passage to the ambient.

2. A potpourri package comprising:
    a carton;
    a bag of potpourri located within said carton,
        said carton having four sides, a bottom, a top and a lid closing said top, said lid formed with an opening centrally disposed therein,
            a top portion of the bag being threaded through said centrally disposed opening in the lid and extending upwardly therefrom,
            the top portion of the bag having a restrictive passageway establishing limited communication between the interior of the bag and the exterior of the carton, a plurality of bottom flaps forming said bottom with each said flap connected to a lower edge of a corresponding one of said sides and said flaps interconnected together with one another and forming a collapsible carton bottom.

3. A potpourri package as set forth in claim 2, further comprising a pleated skirt formed of the top portion of the bag extending from the lid flattened about the lid.

4. A potpourri package as claimed in claim 2, wherein at least one of said four sides of the carton has an opening defining a window.

5. A potpourri package as claimed in claim 2, wherein said lid has a plurality of radial slits at said opening thereby to form a flexible periphery by tabs surrounding the opening.

6. A potpourri package as set forth in claim 2, further comprising a bow tied about the top portion of the bag extending from the lid of the carton.

7. A potpourri package as claimed in claim 2, wherein said carton further includes top side flaps operatively associated with said lid including cooperating cut-outs along edges thereof which form an opening in register with the opening in the lid upon closure of the lid and which passes and surround the top portion of the bag located below the lid.

8. In combination:
    a potpourri package comprising;
    a carton having a top wall thereof formed with a centrally disposed restricted opening therein;
    a bag of scented potpourri inserted in said carton and said bag having an open top which is gathered and threaded through said restricted opening to form a neck in said bag,
        said neck of said bag having a throat extending therethrough forming a passage extending between the interior of the bag and the ambient exteriorly of the carton and through which the scent of the potpourri may be vented to the ambient.

9. A potpourri package for room fragrant potpourri comprising:
    a sheet-form body cut, scored and shaped to form a rectangular tube-like box body having a bottom and a top;
    a wall closing said bottom of said box body;
    a lid and a pair of closure flaps for selectively opening and closing said top of said box body,
        said box body having front, rear and side panels extending between the top and bottom of said tube-like box body;
    a potpourri bag filled with scented potpourri inserted into said carton through said top of the box body,
        said bag being made of material forming transparent walls through which the potpourri contents of the bag may be viewed,
        at least one of said panels having a window formed therein through which the bag and its contents may be viewed through said box body;
    said lid and said closure flaps together with one another each having a restricted opening formed therein and adapted to register with one another when the closure flaps are closed and the lid overlies the closure flaps, said bag having an open top gathered and laced and threaded through said restricted opening to form a confined neck in the bag, said bag being of sufficient length relative to said box body so that the gathered top of the bag forms a skirt overlying said lid;

said confined neck of said bag having a passage extending from the interior of the bag to the ambient exteriorly of the carton through which the scent of the potpourri may be vented.

10. A potpourri package comprising:

a die cut sheet-form body embossed and perforated to provide a rectangular panel section connected at top and bottom edges to top and bottom flap sections, respectively;

rectangular first side, front, second side and back panels formed respectively from a right edge of the panel section by embossed creases separating the panels and adapted to form sides of a carton;

a back panel tab formed adjacent to and to the left of said back panel and adapted to operatively engage an interior surface of said first side panel;

bottom flaps formed in said bottom flap section along bottom edges of said panels and adapted to operatively interconnect with each other to form a bottom for the carton, but being collapsible flat when folded together;

top flaps formed in the top flap section along top edges of the panels, each of the top flaps including a cut-out along a top edge thereof, the top flaps being operatively associated with each other so that upon folding down of the top flaps, the cut-outs register with each other, and together with one another define a first hole;

a lid formed in the top flap section along a top edge of one of the panels, the lid including a second hole defined therein and being operatively associated with the top flaps so that the second hole in said lid registers with the first hole defined by the cut-outs upon closure of the lid;

a potpourri bag in said carton and having an open top gathered and threaded through said first and second holes in said flaps and in said lid to form a confined neck in the bag, said neck having a passage extending from the interior of the bag to the ambient exteriorly of the carton through which the scent of the potpourri in the bag may be vented to ambient.

11. A potpourri package as defined in claim 10, wherein said lid includes a plurality of circumferentially-spaced tabs separated by slits and forming a flexible periphery for said second hole in said lid.

12. A method of packaging fragrant potpourri, comprising the steps of:

filling an open top bag with scented potpourri;

inserting the bag of potpourri into the top of a lidded carton thereby to confine the bag in the carton;

gathering a necked down top portion of the bag;

threading the necked down top portion of the bag through a restricted opening in the lid while closing the lid and thereby form a restricted passageway in the necked down portion communicating between the interior of the bag and the exterior of the carton;

tieing a bow around the protruding neck-down portion of the bag without restricting the passageway in the bag communicating the interior of the bag to the exterior of the carton;

whereby a limited stream of scented fragrance may flow through the passage.

* * * * *